US010214341B2

(12) United States Patent
Nakajima et al.

(10) Patent No.: US 10,214,341 B2
(45) Date of Patent: Feb. 26, 2019

(54) AEROSOL PRODUCT FOR FORMING COOLING GEL COMPOSITION FOR HUMAN BODY (71) Applicant: Toyo Aerosol Industry Co., Ltd., Tokyo (JP)

(72) Inventors: Yasutomo Nakajima, Tokyo (JP); Makoto Tsubouchi, Tokyo (JP); Hokuto Kamijyo, Tokyo (JP); Tomoyuki Niinomi, Tokyo (JP); Remi Ikeda, Tokyo (JP)

(73) Assignee: Toyo Aerosol Industry Co., Ltd., Tokyo (JP)

( * ) Notice: Subject to any disclaimer, the term of this patent is extended or adjusted under 35 U.S.C. 154(b) by 0 days.

(21) Appl. No.: 15/556,344

(22) PCT Filed: Mar. 9, 2016

(86) PCT No.: PCT/JP2016/057300
§ 371 (c)(1),
(2) Date: Sep. 7, 2017

(87) PCT Pub. No.: WO2016/147971
PCT Pub. Date: Sep. 22, 2016

(65) Prior Publication Data
US 2018/0044098 A1  Feb. 15, 2018

(30) Foreign Application Priority Data
Mar. 13, 2015  (JP) ................. 2015-050129

(51) Int. Cl.
A61K 8/04 (2006.01)
A61K 8/34 (2006.01)
A61K 8/41 (2006.01)
A61K 8/60 (2006.01)
A61K 8/73 (2006.01)
A61K 8/81 (2006.01)
C09K 3/30 (2006.01)
C09K 5/16 (2006.01)
A45D 34/00 (2006.01)
A61Q 15/00 (2006.01)
(Continued)

(52) U.S. Cl.
CPC ............. B65D 83/62 (2013.01); A45D 34/00 (2013.01); A61K 8/042 (2013.01); A61K 8/046 (2013.01); A61K 8/34 (2013.01); A61K 8/345 (2013.01); A61K 8/41 (2013.01); A61K 8/60 (2013.01); A61K 8/73 (2013.01); A61K 8/731 (2013.01); A61K 8/8147 (2013.01); A61Q 15/00 (2013.01); A61Q 19/00 (2013.01); B65D 83/68 (2013.01); B65D 83/682 (2013.01); B65D 83/752 (2013.01); C09K 5/16 (2013.01); A45D 2200/057 (2013.01); A61K 2800/244 (2013.01); A61K 2800/87 (2013.01); A61K 2800/88 (2013.01); C09K 3/30 (2013.01)

(58) Field of Classification Search
CPC ...... A61K 2800/87; A61K 8/046; A61K 8/34; A61K 8/345; A61K 2800/244; A61K 2800/88; A61K 2800/882; B65D 83/62; B65D 83/68; B65D 83/682; B65D 83/752; A45D 2200/057; A45D 2200/058; A45D 34/00; A61Q 19/00; A61Q 11/00; A61M 11/006; C09K 3/30
See application file for complete search history.

(56) References Cited

U.S. PATENT DOCUMENTS

2003/0044432 A1  3/2003  Manetta et al.
2003/0108487 A1  6/2003  Bara
(Continued)

FOREIGN PATENT DOCUMENTS

EP  2821060 A1  1/2015
JP  2000087017 A  3/2000
(Continued)

OTHER PUBLICATIONS

JP 2004161292 A, English translation from Espacenet, printed in May 2018.*
(Continued)

Primary Examiner — Mark V Stevens
(74) Attorney, Agent, or Firm — Lucas & Mercanti, LLP (57) ABSTRACT The present invention has as its object the provision of an aerosol product for forming a cooling gel composition for the human body. The aerosol product can easily and stably form a cooling gel composition for the human body which has high storage stability and which provides comfort during use and a sufficient cooling effect.

The aerosol product for forming a cooling gel composition for the human body of the present invention has a double-structure container including a propellant filling space and two liquid concentrate filling spaces and having a discharging mechanism for simultaneously discharging the contents filled in these two liquid concentrate filling spaces. The propellant filling space is filled with a propellant composed of a compressed gas. A first liquid concentrate filling space is filled with a first liquid concentrate composition containing a hydrated endothermic substance dispersed in a liquid medium. A second liquid concentrate filling space contains a second liquid concentrate composition containing water. The first liquid concentrate composition and the second liquid concentrate composition, which have a viscosity of 1,000 to 125,000 mPa·s at a temperature of 20° C., are mixed to form a cooling gel composition for the human body.

6 Claims, 2 Drawing Sheets (51) Int. Cl.
*A61Q 19/00* (2006.01)
*B65D 83/14* (2006.01)
*B65D 83/62* (2006.01)
*B65D 83/68* (2006.01)

(56) References Cited

U.S. PATENT DOCUMENTS

| | | |
|---|---|---|
| 2005/0205086 A1 | 9/2005 | Tamarkin et al. |
| 2009/0264839 A1* | 10/2009 | Kriksunov ........... A61K 9/0014 604/290 |
| 2014/0246515 A1 | 9/2014 | Nakajima |

FOREIGN PATENT DOCUMENTS

| | | | |
|---|---|---|---|
| JP | 2001031520 A * | 2/2001 | |
| JP | 2004161292 A * | 6/2004 | ............. B65D 83/62 |
| JP | 2004285052 A | 10/2004 | |
| JP | 2008214277 A | 9/2008 | |
| KR | 10-1140416 B1 | 5/2012 | |
| WO | 2013062190 A1 | 5/2013 | |

OTHER PUBLICATIONS

JP 2001031520 A, English translation from Google, printed in May 2018.*
International Search Report dated Apr. 5, 2016 for PCT/JP2016/057300.
Extended European Search Report dated Dec. 6, 2017 from corresponding European Application No. 16764801.3.
Office Action dated Oct. 29, 2018 from Korean Application No. 10-2017-7028214 and English translation.

* cited by examiner

AEROSOL PRODUCT FOR FORMING COOLING GEL COMPOSITION FOR HUMAN BODY

CROSS REFERENCE TO RELATED APPLICATION

This Application is a 371 of PCT/JP2016/057300 filed on Mar. 9, 2016 which, in turn, claimed the priority of Japanese Patent Application No. 2015-050129 filed Mar. 13, 2015, both applications are incorporated herein by reference.

TECHNICAL FIELD

The present invention relates to an aerosol product for forming a cooling gel composition for the human body.

BACKGROUND ART

In the related art, cooling agents for the human body contain various cooling components (see, for example, Patent Literature 1).

Specifically, some cooling agent compositions used in cooling agents for the human body contain menthol as a cooling component. To obtain a sufficient cooling effect from menthol, cooling agent compositions need to contain a large amount of menthol, which may cause a problem of skin irritation at an application site.

Since a cooling agent composition in a cooling agent produced by filling an aerosol container with the cooling agent composition is discharged together with a propellant, the heat of vaporization of the propellant at an application site instantaneously produces excessive cooling sensation and thus provides an undesired cooling effect, which is problematic.

Some other cooling agents for the human body contain, as a cooling component, a hydrated endothermic substance, such as a sugar alcohol (specifically, erythritol, xylitol, or the like). The hydrated endothermic substance causes a chemical reaction or a physical reaction to absorb heat when brought into contact with water. This cooling agent exerts a cooling effect via an endothermic reaction generated by contact between the hydrated endothermic substance and sweat.

However, cooling agents for the human body containing a hydrated endothermic substance as a cooling component do not cause skin irritation but fail to provide a stable, sufficient cooling effect because sweat induces the endothermic reaction of the hydrated endothermic substance in the cooling agent. In addition to this problem, there is another problem in that it is difficult to stably store sugar alcohols for a long period of time because sugar alcohols are hygroscopic.

CITATION LIST

Patent Literature

Patent Literature 1: Japanese Patent Application Laid-Open No. 2000-087017

SUMMARY OF INVENTION

Technical Problem

The present invention has been made in view of the foregoing circumstances and has as its object the provision of an aerosol product of an aerosol dispenser for forming a cooling gel composition for the human body. The aerosol product can easily and stably form a cooling gel composition for the human body which has high storage stability and which provides comfort during use and a sufficient cooling effect.

Solution to Problem

An aerosol product for forming a cooling gel composition for the human body of the present invention has a double-structure container including a propellant filling space and two independent liquid concentrate filling spaces and having a discharging mechanism for simultaneously discharging contents filled in the two liquid concentrate filling spaces, the propellant filling space in the double-structure container is filled with a propellant composed of a compressed gas, a first liquid concentrate filling space in the double-structure container is filled with a first liquid concentrate composition, and a second liquid concentrate filling space in the double-structure container is filled with a second liquid concentrate composition, the first liquid concentrate composition contains a hydrated endothermic substance dispersed in a liquid medium composed of a solvent containing a viscosity modifier and has a viscosity of 1,000 to 125,000 mPa·s at a temperature of 20° C., the second liquid concentrate composition contains water and a viscosity modifier and has a viscosity of 1,000 to 125,000 mPa·s at a temperature of 20° C., and the first liquid concentrate composition discharged from the first liquid concentrate filling space and the second liquid concentrate composition discharged from the second liquid concentrate filling space are mixed to form a cooling gel composition for the human body.

In the aerosol product for forming a cooling gel composition for the human body of the present invention, the mixing ratio of the first liquid concentrate composition to the second liquid concentrate composition (the mass of the first liquid concentrate composition:the mass of the second liquid concentrate composition) discharged from the discharging mechanism may preferably be from 0.8:1.2 to 1.2:0.8.

In the aerosol product for forming a cooling gel composition for the human body of the present invention, the hydrated endothermic substance contained in the first liquid concentrate composition may preferably be at least one selected from the group consisting of xylitol, sorbitol, erythritol, maltitol, lactitol, mannitol and palatinit.

In the aerosol product for forming a cooling gel composition for the human body of the present invention, the content ratio of the hydrated endothermic substance in the first liquid concentrate composition may preferably be 1% to 30% by mass per 100% by mass of the first liquid concentrate composition.

Advantageous Effects of Invention

The aerosol product for forming a cooling gel composition for the human body of the present invention has a double-structure container having a discharging mechanism for simultaneously discharging the contents filled in two liquid concentrate filling spaces. One of the two liquid concentrate filling spaces is filled with a first liquid concentrate composition having a particular viscosity and containing a hydrated endothermic substance dispersed in a liquid medium composed of a solvent containing a viscosity modifier. The other is filled with a second liquid concentrate composition having a particular viscosity and containing water and a viscosity modifier.

Since the hydrated endothermic substance is always uniformly dispersed in the liquid medium in the first liquid concentrate composition, mixing the first liquid concentrate composition and the second liquid concentrate composition allows the hydrated endothermic substance that uniformly exists to evenly exert a suitable cooling effect. The hydrated endothermic substance that exerts such a cooling effect has no risk of skin irritation. Since the first liquid concentrate composition and the second liquid concentrate composition can be simultaneously discharged in suitable amounts from the two liquid concentrate filling spaces in the double-structure container, respectively, the first liquid concentrate composition and the second liquid concentrate composition can always be mixed in a constant quantitative ratio. As a result, there is no possibility that the amount of one liquid concentrate composition discharged is much larger than the amount of another liquid concentrate composition discharged. In addition, the propellant is not discharged together with the first liquid concentrate composition and the second liquid concentrate composition from the double-structure container, so that instantaneous, excessive cooling sensation due to vaporization of the propellant is not produced at an application site. As a result, a desired cooling effect controlled by, for example, the content ratio of the hydrated endothermic substance in the first liquid concentrate composition can be obtained.

Moreover, the long-term storage stability can be obtained because neither the first liquid concentrate composition nor the second liquid concentrate composition is exposed to the air outside the container.

Therefore, the aerosol product for forming a cooling gel composition for the human body of the present invention can easily and stably form a cooling gel composition for the human body which has high storage stability and which provides comfort during use and a sufficient cooling effect.

DESCRIPTION OF EMBODIMENTS

An aerosol product for forming a cooling gel composition for the human body of the present invention has a double-structure container including a propellant filling space and two independent liquid concentrate filling spaces and having a discharging mechanism for simultaneously discharging the contents filled in these two liquid concentrate filling spaces. In this double-structure container, the propellant filling space is filled with a propellant composed of a compressed gas. A first liquid concentrate filling space is filled with a first liquid concentrate composition containing a hydrated endothermic substance, and a second liquid concentrate filling space is filled with a second liquid concentrate composition containing water.

In the aerosol product for forming a cooling gel composition for the human body of the present invention, the first liquid concentrate composition and the second liquid concentrate composition simultaneously discharged from the first liquid concentrate filling space and the second liquid concentrate filling space, respectively, are mixed to form a cooling gel composition for the human body. In the cooling gel composition for the human body, the hydrated endothermic substance is caused to react with water. Because of the reaction between the hydrated endothermic substance and water, the hydrated endothermic substance absorbs heat to provide a cooling effect.

First Liquid Concentrate Composition:

The first liquid concentrate composition is a liquid containing a hydrated endothermic substance dispersed in a liquid medium composed of a solvent containing a viscosity modifier.

As long as at least part of the hydrated endothermic substance is dispersed in the first liquid concentrate composition, part of the hydrated endothermic substance may be dissolved in the liquid medium. In other words, the first liquid concentrate composition needs to contain the hydrated endothermic substance in an amount more than the saturation solubility in the liquid medium.

Examples of the solvent, which is an essential component of the first liquid concentrate composition, include water and alcohols. These may be used either singly or in any combination thereof.

Specific examples of water used in the first liquid concentrate composition include purified water and ion-exchanged water.

Specific examples of the alcohol used in the first liquid concentrate composition include ethanol.

The content ratio of the solvent may preferably be 60% by mass or more per 100% by mass of the first liquid concentrate composition in consideration of, for example, the relationship with the content ratios of other components.

Examples of the viscosity modifier that is an essential component of the first liquid concentrate composition include a thickener, such as a cellulose derivative, xanthan gum, and a carboxyvinyl polymer.

These may be used either singly or in any combination thereof.

The content ratio of the viscosity modifier may preferably be 0.05% to 10% by mass per 100% by mass of the first liquid concentrate composition.

If the content ratio of the viscosity modifier is too high, sticky feeling or the like may be caused instead of comfort during use.

If the content ratio of the viscosity modifier is too low, the first liquid concentrate composition may fail to have sufficient dispersion stability of the hydrated endothermic substance. In addition, dripping may occur at an application site.

The hydrated endothermic substance, which is an essential component of the first liquid concentrate composition, is a substance that causes a chemical reaction or a physical reaction to absorb heat when brought into contact with water.

The hydrated endothermic substance may preferably be a sugar alcohol. The sugar alcohol that constitutes a hydrated endothermic substance may preferably be at least one selected from the group consisting of xylitol, sorbitol, erythritol, maltitol, lactitol, mannitol, and palatinit.

In the first liquid concentrate composition, the content ratio of the hydrated endothermic substance is appropriately set according to, for example, the type of solvent, the degree of cooling effect required depending on the intended use of the aerosol product for forming a cooling gel composition for the human body, and the type of hydrated endothermic substance. The content ratio of the hydrated endothermic substance may preferably be 1% to 30% by mass, more preferably 5% to 30% by mass per 100% by mass of the first liquid concentrate composition.

The first liquid concentrate composition may contain optional components as desired, in addition to the essential components (specifically, the solvent, the viscosity modifier, and the hydrated endothermic substance).

Examples of the optional components include a preservative, a pH adjuster, a coloring agent, a flavor, and components (for example, active ingredients) required depending on the intended use of the aerosol product for forming a cooling gel composition for the human body.

The first liquid concentrate composition constituted by the essential components and the optional components as described above needs to have a viscosity of 1,000 to 125,000 mPa·s, preferably 1,000 to 50,000 mPa·s at a temperature of 20° C.

If the viscosity of the first liquid concentrate composition is too high, it is difficult to discharge the first liquid concentrate composition. In addition, the first liquid concentrate composition may not be discharged in a desired amount associated with the amount of the second liquid concentrate composition discharged.

If the viscosity of the first liquid concentrate composition is too low, the hydrated endothermic substance may fail to have sufficient dispersion stability, and dripping may occur at an application site. In addition, the first liquid concentrate composition may not be discharged in a desired amount associated with the amount of the second liquid concentrate composition discharged.

Second Liquid Concentrate Composition:

The second liquid concentrate composition is a liquid containing water and a viscosity modifier as essential components.

Specific examples of water, which is an essential component of the second liquid concentrate composition, include purified water and ion-exchanged water.

The content ratio of water may preferably be 50% to 95% by mass per 100% by mass of the second liquid concentrate composition.

If the content ratio of water is too high, the second liquid concentrate composition may not contain a sufficient ratio of the viscosity modifier.

If the content ratio of water is too low, the cooling gel composition for the human body formed may not have a sufficient cooling effect.

Examples of the viscosity modifier that is an essential component of the second liquid concentrate composition include a thickener, such as a cellulose derivative, xanthan gum, and a carboxyvinyl polymer.

These may be used either singly or in any combination thereof.

The content ratio of the viscosity modifier may preferably be 0.05% to 5% by mass per 100% by mass of the second liquid concentrate composition.

If the content ratio of the viscosity modifier is too high, sticky feeling or the like may be caused instead of comfort during use.

If the content ratio of the viscosity modifier is too low, dripping may occur at an application site.

The second liquid concentrate composition may contain optional components as desired, in addition to the essential components (specifically, water and the viscosity modifier).

Examples of the optional components include an alcohol, a preservative, a pH adjuster, a coloring agent, a flavor, and components (for example, active ingredients) required depending on the intended use of the aerosol product for forming a cooling gel composition for the human body.

The second liquid concentrate composition constituted by the essential components and the optional components as described above needs to have a viscosity of 1,000 to 125,000 mPa·s, preferably 1,000 to 50,000 mPa·s at a temperature of 20° C.

If the viscosity of the second liquid concentrate composition is too high, it is difficult to discharge the second liquid concentrate composition. In addition, the second liquid concentrate composition may not be discharged in a desired amount associated with the amount of the first liquid concentrate composition discharged.

If the viscosity of the second liquid concentrate composition is too low, dripping may occur at an application site. In addition, the second liquid concentrate composition may not be discharged in a desired amount associated with the amount of the first liquid concentrate composition discharged.

Propellant:

A compressed gas is used as a propellant.

Examples of the compressed gas include nitrous oxide gas, nitrogen gas, carbon dioxide gas and a mixture of these gases.

This propellant is not discharged from the propellant filling space into the outside of the double-structure container along with simultaneous discharge of the first liquid concentrate composition and the second liquid concentrate composition.

The propellant may preferably be enclosed such that the pressure applied when the double-structure container is filled with the propellant is 0.3 to 1.2 MPa at 25° C.

If the pressure applied when the double-structure container is filled with the propellant (product inner pressure) is too high or too low, in both cases, the contents may not be sprayed in favorable conditions.

Double-Structure Container:

The double-structure container of the aerosol product for forming a cooling gel composition for the human body of the present invention includes a propellant filling space to be filled with a propellant, a first liquid concentrate filling space to be filled with a first liquid concentrate composition, and a second liquid concentrate filling space to be filled with a second liquid concentrate composition. The double-structure container further includes a discharging mechanism for simultaneously discharging the first liquid concentrate composition and the second liquid concentrate composition from the first liquid concentrate filling space and the second liquid concentrate filling space, respectively.

Figure 1:
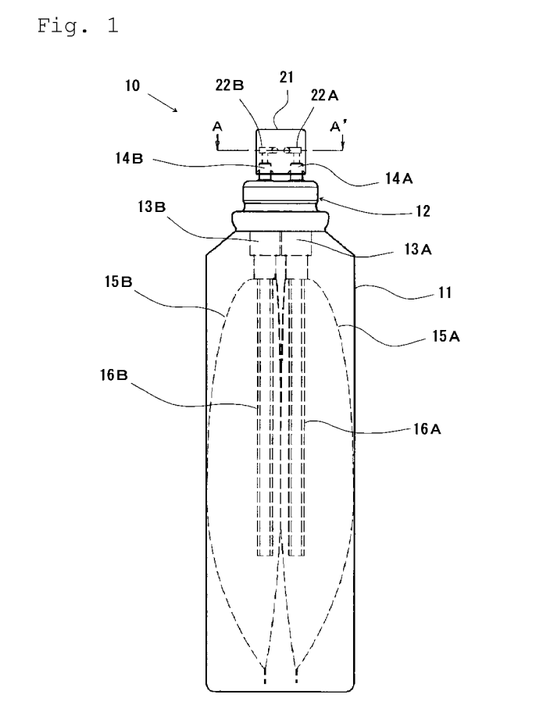
FIG. 1 is an explanatory view illustrating an example structure of a double-structure container used for an aerosol product for forming a cooling gel composition for the human body of the present invention.
Figure 2:
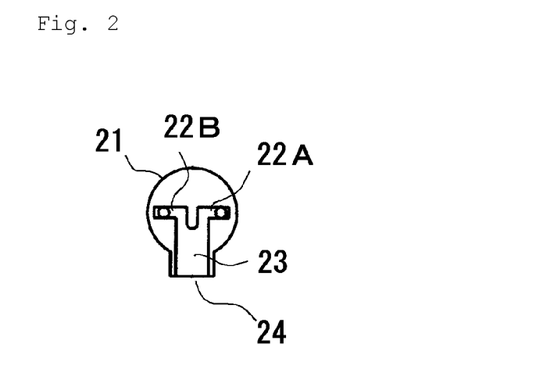
FIG. 2 is a sectional view illustrating a cross section taken along A-A' in FIG. 1.
Figure 3:
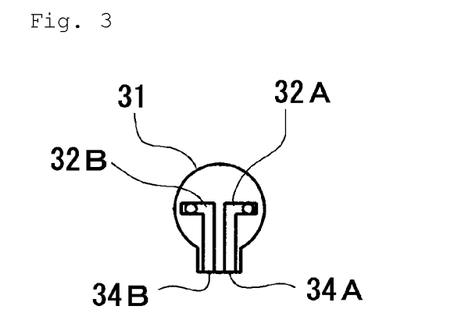
FIG. 3 is an explanatory view illustrating another example structure of a double-structure container used for an aerosol product for forming a cooling gel composition for the human body of the present invention.

Specific examples of the double-structure container according to the present invention include the following two containers illustrated in FIG. 1 to FIG. 3.

FIG. 1 is an explanatory view illustrating an example structure of the double-structure container used for the aerosol product for forming a cooling gel composition for the human body. FIG. 2 is a sectional view illustrating a cross section taken along A-A' in FIG. 1.

This double-structure container 10 includes a pressure resistant container 11 made of metal and provided with an aerosol valve 12. The pressure resistant container 11 is provided thereinside with a first inner bag 15A that is formed of, for example, an aluminum laminated film and that defines a first liquid concentrate filling space to be filled with the first liquid concentrate composition, and a second inner bag 15B that is formed of, for example, an aluminum laminated film and that defines a second liquid concentrate filling space to be filled with the second liquid concentrate composition. In the pressure resistant container 11, a propellant filling space to be filled with the propellant is formed from a gap defined by the pressure resistant container 11, the first inner bag 15A, and the second inner bag 15B. The aerosol valve 12 is provided with a first stem 14A and a second stem 14B each having a stem passage inside. The first stem 14A and the second stem 14B are disposed to be movable up and down inside a first housing 13A and a second housing 13B, respectively. A common actuator 21 is disposed on the upper ends of the first stem 14A and the second stem 14B.

In the example illustrated in the figure, a reference character 16A denotes a first dip tube in communication with the stem passage in the first stem 14A at the lower end of the first housing 13A. The first dip tube 16A extends inside the first inner bag 15A toward the bottom of the pressure resistant container 11. A reference character 16B denotes a second dip tube in communication with the stem passage in the second stem 14B at the lower end of the second housing 13B. The second dip tube 16B extends inside the second inner bag 15B toward the bottom of the pressure resistant container 11.

In FIG. 1, the components located inside the pressure resistant container 11 and the actuator 21 are drawn with broken lines.

The common actuator 21 contains a first actuator passage 22A in communication with the stem passage in the first stem 14A, a second actuator passage 22B in communication with the stem passage in the second stem 14B, and a discharge space 23 in communication with, at its end, the first actuator passage 22A and the second actuator passage 22B and forming, at its another end, a discharge port 24.

The actuator 21 common to the first stem 14A for the first inner bag 15A and the second stem 14B for the second inner bag 15B is provided accordingly so as to form the discharging mechanism for simultaneously discharging the first liquid concentrate composition filled in the first inner bag 15A and the second liquid concentrate composition filled in the second inner bag 15B from the first inner bag 15A and the second inner bag 15B, respectively.

In the double-structure container 10 having such a structure, the first inner bag 15A is filled with the first liquid concentrate composition, the second inner bag 15B is filled with the second liquid concentrate composition, and the propellant filling space is filled with a propellant. The inside of the pressure resistant container 11 is always pressurized with the propellant accordingly. Therefore, when the actuator 21 is actuated (depressed), the pressure of the propellant shrinks the first inner bag 15A and the second inner bag 15B, which causes the first liquid concentrate composition and the second liquid concentrate composition to be discharged simultaneously from the first inner bag 15A and the second inner bag 15B, respectively. As a result, the first liquid concentrate composition and the second liquid concentrate composition are discharged from the discharge port 24 of the actuator 21.

Specifically, while the actuator 21 is not actuated or depressed in the double-structure container 10 filled with the first liquid concentrate composition, the second liquid concentrate composition, and the propellant, the first stem 14A and the second stem 14B are being pushed up to block the stem passage in the first stem 14A and the stem passage in the second stem 14B from the inside of the pressure resistant container 11. While the actuator 21 is actuated or depressed, the first stem 14A and the second stem 14B are pushed down, so that the stem passage in the first stem 14A and the stem passage in the second stem 14B simultaneously communicate with the inside of the pressure resistant container 11. The first liquid concentrate composition in the first inner bag 15A and the second liquid concentrate composition in the second inner bag 15B are discharged simultaneously through the fluid passages formed by the first dip tube 16A and the second dip tube 16B, respectively. The first liquid concentrate composition and the second liquid concentrate composition thus simultaneously discharged reach the discharge space 23 through the stem passage in the first stem 14A and the stem passage in the second stem 14B and through the first actuator passage 22A and the second actuator passage 22B, respectively. The first liquid concentrate composition and the second liquid concentrate composition are discharged from the discharge port 24 without being mixed during passage through the discharge space 23. The first liquid concentrate composition and the second liquid concentrate composition discharged from the discharge port 24 are mixed with, for example, the fingers at an application site or the like to form a cooling gel composition for the human body.

FIG. 3 is an explanatory view illustrating another example structure of the double-structure container used for the aerosol product for forming a cooling gel composition for the human body of the present invention. Specifically, FIG. 3 is an explanatory sectional view illustrating the structure of an actuator in accordance with the double-structure container.

This double-structure container has the same structure as that of the double-structure container 10 in accordance with FIG. 1 and FIG. 2 except that the actuator 21 is replaced by an actuator 31 having two discharge ports (specifically, a first discharge port 34A and a second discharge port 34B) and configured such that the first liquid concentrate composition and the second liquid concentrate composition are separately discharged from these two discharge ports, respectively.

In other words, the double-structure container in accordance with FIG. 3 includes the actuator 31 and a pressure resistant container having the same structure as that of the pressure resistant container 11 constituting the double-structure container 10 in accordance with FIG. 1 and FIG. 2.

The actuator 31 is provided with a first actuator passage 32A in communication with, at one end, the stem passage in the first stem and forming a first discharge port 34A at another end, and a second actuator passage 32B in communication with, at one end, the stem passage in the second stem and forming a second discharge port 34B at another end.

The actuator 31 is an actuator common to the first stem and the second stem and is disposed at the upper ends of the first stem and the second stem, like the actuator 21 in the double-structure container 10 in accordance with FIG. 1 and FIG. 2.

While the actuator 31 is actuated or depressed in the double-structure container having such a structure and filled with the first liquid concentrate composition, the second liquid concentrate composition, and the propellant, the first liquid concentrate composition in the first inner bag and the second liquid concentrate composition in the second inner bag are discharged simultaneously. The first liquid concentrate composition is discharged from the first discharge port 34A through the stem passage in the first stem in the aerosol valve and through the first actuator passage 32A, whereas the second liquid concentrate composition is discharged from the second discharge port 34B through the stem passage in the second stem in the aerosol valve and through the second actuator passage 32B. The first liquid concentrate composition and the second liquid concentrate composition discharged from the first discharge port 34A and the second discharge port 34B, respectively, are mixed with, for example, the fingers at an application site or the like to form a cooling gel composition for the human body.

In the double-structure container having the structure described above, the discharging mechanism enables the first liquid concentrate composition filled in the first liquid concentrate filling space and the second liquid concentrate composition filled in the second liquid concentrate filling space to be discharged simultaneously. The discharging mechanism further enables the amount of the first liquid concentrate composition discharged from the first liquid concentrate filling space and the amount of the second liquid concentrate composition discharged from the second liquid concentrate filling space to be controlled at an appropriate quantitative ratio, specifically, so as to be substantially the same.

In the aerosol product for forming a cooling gel composition for the human body of the present invention, the mixing ratio of the first liquid concentrate composition discharged from the first liquid concentrate filling space to the second liquid concentrate composition discharged from the second liquid concentrate filling space (the mass of the first liquid concentrate composition:the mass of the second liquid concentrate composition) may preferably be from 0.8:1.2 to 1.2:0.8.

In other words, the amount of the first liquid concentrate composition discharged from the first liquid concentrate filling space and the amount of the second liquid concentrate composition discharged from the second liquid concentrate filling space each may preferably fall within a range of ±20% of the mean of the amounts of the first liquid concentrate composition discharged and the second liquid concentrate composition discharged.

The mixing ratio (the mass of the first liquid concentrate composition:the mass of the second liquid concentrate composition) can be controlled within the above-described range by setting, for example, the viscosity of the first liquid concentrate composition at a temperature of 20° C. to 1,000 to 125,000 mPa·s, and the viscosity of the second liquid concentrate composition at a temperature of 20° C. to 1,000 to 125,000 mPa·s.

If the mixing ratio (the mass of the first liquid concentrate composition:the mass of the second liquid concentrate composition) is out of the above-described range, the amount of the first liquid concentrate composition discharged from the first liquid concentrate filling space is significantly different from the amount of the second liquid concentrate composition discharged from the second liquid concentrate filling space. Therefore, the cooling gel composition for the human body formed by mixing the first liquid concentrate composition and the second liquid concentrate composition may not have a desired cooling effect.

The aerosol product for forming a cooling gel composition for the human body of the present invention described above is produced by filling the first liquid concentrate filling space and the second liquid concentrate filling space in the double-structure container with the first liquid concentrate composition and the second liquid concentrate composition, respectively, and filling the propellant filling space with the propellant.

The aerosol product for forming a cooling gel composition for the human body of the present invention has a double-structure container having a discharging mechanism for simultaneously discharging the contents filled in two liquid concentrate filling spaces. One of the two liquid concentrate filling spaces is filled with a first liquid concentrate composition having a particular viscosity and containing a hydrated endothermic substance dispersed in a liquid medium composed of a solvent containing a viscosity modifier. The other is filled with a second liquid concentrate composition having a particular viscosity and containing water and a viscosity modifier.

Since the hydrated endothermic substance is always uniformly dispersed in the liquid medium in the first liquid concentrate composition, mixing the first liquid concentrate composition and the second liquid concentrate composition allows the hydrated endothermic substance that uniformly exists to evenly exert a suitable cooling effect. The hydrated endothermic substance that exerts such a cooling effect has no risk of skin irritation, unlike menthol or other substances. Since the first liquid concentrate composition and the second liquid concentrate composition can be discharged simultaneously in suitable amounts (specifically, in the same amount) from the two liquid concentrate filling spaces in the double-structure container, respectively, the first liquid concentrate composition and the second liquid concentrate composition can always be mixed in a constant quantitative ratio, and there is no possibility that the amount of one liquid concentrate composition discharged is much larger than the amount of another liquid concentrate composition discharged. In addition, the propellant is not discharged together with the first liquid concentrate composition and the second liquid concentrate composition from the double-structure container, so that instantaneous, excessive cooling sensation due to vaporization of the propellant is not produced at an application site. As a result, a cooling gel composition for the human body that provides comfort during use and has a desired cooling effect controlled by, for example, the content ratio of the hydrated endothermic substance in the first liquid concentrate composition can always be formed easily by simply operating the discharging mechanism, specifically, for example, only depressing the actuator once (one push) to discharge the first liquid concentrate composition and the second liquid concentrate composition.

Moreover, the long-term storage stability can be obtained because neither the first liquid concentrate composition nor the second liquid concentrate composition is exposed to the air outside the container, which prevents the moisture absorption of the hydrated endothermic substance which usually has high hygroscopicity.

Therefore, the aerosol product for forming a cooling gel composition for the human body of the present invention can easily and stably form a cooling gel composition for the human body which has high storage stability and which provides comfort during use and a sufficient cooling effect.

In the aerosol product for forming a cooling gel composition for the human of the present invention, a non-flammable compressed gas is used as a propellant for the first liquid concentrate composition and the second liquid concentrate composition. The use of the non-flammable compressed gas provides high safety irrespective of the operation environment and eliminates the risk of an explosion accident in discarding the double-structure container.

For the aerosol product for forming a cooling gel composition for the human body of the present invention having either an actuator illustrated in FIG. 2 or an actuator illustrated in FIG. 3, the user can enjoy the process for forming the cooling gel composition for the human body by mixing the first liquid concentrate composition and the second liquid concentrate composition at an application site or can enjoy changes in the state of a mixture of the first liquid concentrate composition and the second liquid concentrate composition.

The aerosol product for forming a cooling gel composition for the human body of the present invention as described above is used as a cooling agent. The aerosol product, however, can be used in various applications for the human body when it contains optional components (specifically, for example, active ingredients) as desired. Specifically, the aerosol product can be used as a cosmetic lotion, a facial mask, or the like.

EXAMPLES

Examples of the present invention will be described below, but the present invention is not limited by these.

Example 1

Preparation of First Liquid Concentrate Composition:
A first liquid concentrate composition was prepared by mixing the components described below.

The viscosity of the obtained first liquid concentrate composition at a temperature of 20° C. was measured using a BM-type rotary viscometer (rotor No. 4, 60 rpm, after 1 minute) and found to be 7,500 mPa·s.
Constituents of First Liquid Concentrate Composition:
Erythritol: 24.0% by mass
Carboxyvinyl polymer: 0.2% by mass
Triethanolamine: 0.2% by mass
Purified water: 37.8% by mass
Ethanol: 37.8% by mass
Total: 100.0% by mass
Preparation of Second Liquid Concentrate Composition:
A second liquid concentrate composition was prepared by mixing the components described below.

The viscosity of the obtained second liquid concentrate composition at a temperature of 20° C. was measured using a BM-type rotary viscometer (rotor No. 4, 60 rpm, after 1 minute) and found to be 5,000 mPa·s.
Constituents of Second Liquid Concentrate Composition:
Carboxyvinyl polymer: 0.2% by mass
Triethanolamine: 0.2% by mass
Purified water: 49.8% by mass
Ethanol: 49.8% by mass
Total: 100.0% by mass
Production of Aerosol Product:
An aerosol product for forming a cooling gel composition for the human body for use as a cooling agent was produced by: preparing a double-structure container having the structure illustrated in FIG. 1 and FIG. 2; filling a first liquid concentrate filling space (first inner bag) in the double-structure container with the first liquid concentrate composition; filling a second liquid concentrate filling space (second inner bag) with the second liquid concentrate composition; and filling a propellant filling space with nitrogen gas as a propellant such that the product inner pressure in the double-structure container was 0.7 MPa at 25° C.

The aerosol product for forming a cooling gel composition for the human body in Example 1 was applied several times just after production. As a result, it was found that the aerosol product stably formed a gel composition for the human body that provided comfort without skin irritation during use and had a sufficient cooling effect.

It was also found that, even after storage in an environment at a temperature of 45° C. for a long period of time or for one month, the aerosol product for forming a cooling gel composition for the human body in Example 1 stably formed a gel composition for the human body that provided comfort during use and a sufficient cooling effect that were similar to those obtained just after production.

REFERENCE SIGNS LIST 10 double-structure container
11 pressure resistant container
12 aerosol valve
13A first housing
13B second housing
14A first stem
14B second stem
15A first inner bag
15B second inner bag
16A first dip tube
16B second dip tube
21 actuator
22A first actuator passage
22B second actuator passage
23 discharge space
24 discharge port
31 actuator
32A first actuator passage
32B second actuator passage
34A first discharge port
34B second discharge port

The invention claimed is:
1. An aerosol product for forming a cooling gel composition for a human body, comprising:
a double-structure container including a propellant filling space and two independent liquid concentrate filling spaces and having a discharging mechanism for simultaneously discharging contents of the two liquid concentrate filling spaces, wherein
the propellant filling space in the double-structure container comprises a propellant composed of a compressed gas,
a first liquid concentrate filling space of the two independent liquid concentrate filling spaces in the double-structure container is filled with a first liquid concentrate composition, and a second liquid concentrate filling space of the two independent liquid concentrate filling spaces in the double-structure container is filled with a second liquid concentrate composition,
the first liquid concentrate composition contains a hydrated endothermic substance dispersed in a liquid medium composed of a solvent containing a viscosity modifier and has a viscosity of 1,000 to 125,000 mPa·s at a temperature of 20° C., the hydrated endothermic substance contained in the first liquid concentrate composition comprises at least one selected from the group consisting of xylitol, sorbitol, erythritol, maltitol, lactitol, mannitol, and palatinit, a content ratio of the hydrated endothermic substance in the first liquid concentrate composition is 1% to 30% by mass per 100% by mass of the first liquid concentrate composition, a content ratio of the solvent in the first liquid concentrate composition is 60% by mass or more per 100% by mass of the first liquid concentrate composition, a content ratio of the viscosity modifier in the first liquid concentrate composition is 0.05% to 10% by mass per 100% by mass of the first liquid concentrate composition;

the second liquid concentrate composition contains water and a viscosity modifier and has a viscosity of 1,000 to 125,000 mPa·s at a temperature of 20° C., a content ratio of water in the second liquid concentrate composition is 49.8% to 95% by mass per 100% by mass of the second liquid concentrate composition, a content ratio of the viscosity modifier in the second liquid concentrate composition is 0.05% to 5% by mass per 100% by mass of the second liquid concentrate composition, and the first liquid concentrate composition discharged from the first liquid concentrate filling space and the second liquid concentrate composition discharged from the second liquid concentrate filling space are mixed to form a cooling gel composition for the human body.

2. The aerosol product for forming a cooling gel composition for the human body according to claim 1, wherein a mixing ratio of the first liquid concentrate composition to the second liquid concentrate composition (a mass of the first liquid concentrate composition: a mass of the second liquid concentrate composition) discharged from the discharging mechanism is from 0.8:1.2 to 1.2:0.8.

3. The aerosol product for forming a cooling gel composition for the human body according to claim 1, wherein the container contains a valve, the valve comprising:
    a first housing and a second housing; and
    a first stem and a second stem,
wherein the first stem and the second stem are disposed to be movable up and down inside the first housing and the second housing, respectively, and
the first liquid concentrate filling space and the second liquid concentrate filling space are connected to the first housing and the second housing, respectively.

4. The aerosol product for forming a cooling gel composition for the human body according to claim 3, wherein the first housing and the second housing extend from the valve into the container.

5. The aerosol product for forming a cooling gel composition for the human body according to claim 1, wherein the liquid concentrate filling spaces are two separate bags.

6. The aerosol product for forming a cooling gel composition for the human body according to claim 5, wherein each of the bags is formed from an aluminum laminated film.

* * * * *